United States Patent [19]
Vargas, III

[11] Patent Number: 5,468,245
[45] Date of Patent: Nov. 21, 1995

[54] BIOMEDICAL CEMENT BONDING ENHANCER

[76] Inventor: Joseph H. Vargas, III, 3 Albert Cree Dr., Rutland, Vt. 05701

[21] Appl. No.: 191,105

[22] Filed: Feb. 3, 1994

[51] Int. Cl.⁶ .................................................. A61B 17/56
[52] U.S. Cl. ............................. 606/94; 606/95; 606/192
[58] Field of Search .................... 606/94, 95, 93, 606/92, 99, 102, 86, 191–199; 604/96, 97, 99, 98, 103, 187, 218, 219, 240, 241

[56] References Cited

U.S. PATENT DOCUMENTS

| | | | |
|---|---|---|---|
| 563,621 | 7/1896 | Schimmel | 604/241 |
| 3,889,665 | 6/1975 | Ling et al. | 606/94 |
| 4,293,962 | 10/1981 | Fuson | 606/95 |
| 4,399,814 | 8/1983 | Pratt, Jr. et al. | 606/92 |
| 4,444,188 | 4/1984 | Bazell et al. | 606/194 |
| 4,462,394 | 7/1984 | Jacobs | 606/92 |
| 4,488,549 | 12/1984 | Lee et al. | 606/94 |
| 4,555,242 | 11/1985 | Saudagar | 604/96 |
| 4,627,434 | 12/1986 | Murray | 606/94 |
| 5,147,299 | 9/1992 | Mendoza et al. | 604/96 |
| 5,147,366 | 9/1992 | Arroyo et al. | 606/94 |

FOREIGN PATENT DOCUMENTS

3835853  4/1990  Germany .............................. 606/95

*Primary Examiner*—Stephen C. Pellegrino
*Assistant Examiner*—Guy V. Tucker
*Attorney, Agent, or Firm*—John J. Welch

[57] ABSTRACT

A method and apparatus for filling a shaft bored into human femoral bone during hip replacement surgery with gelatinous methyl methacrylate bonding cement for receipt of an artificial hip prothesis so as to maximally preventing loosening of the prosthesis after hardening of the cement consisting of a cylindrically shaped syringe gun unit screwed into a cylindrically shaped hollow head of a hollow cylindrical applicator tube to the exterior of which applicator tube near its tip there is affixed an inflatable balloon amenable to receipt of fluid by way of tubing passing through a distinct lumen of said applicator tube which said tubing is attached at one end to a hollow canal in the applicator tube leading via the lumen to the balloon and attached at its other end to a valvular component in turn attached to the cylindrical base of a second syringe gun unit which said apparatus serves to facilitate injection of such cement incrementally into relatively air tight spaces within such shaft formed in view of the inflatibility of such balloon until such shaft is completely filled with such cement.

11 Claims, 7 Drawing Sheets

BIOMEDICAL CEMENT BONDING ENHANCER

BACKGROUND OF THE INVENTION

1. Field of the Invention

The instant invention is one of those devices that serves to facilitate the implantation of anticipated hip protheses into the long leg bone of human beings.

Invariably, the primary difficulty with total hip joint replacement procedures as currently performed by orthopaedic surgeons is the tendency of such devices once implanted in human bone to loosen in-situ with the passage of time. For patients who are confronted with such a phenomenon, the choice is simple though unpalatable, namely corrective surgery to be performed in order to alleviate the perambulatory and other problems such as pain and/or discomfort that result from such loosening. It has been demonstrated through studies that there is as much as a 40% loosening rate with respect to such devices per roughly ten year terms of implantation. For reasons that will soon be articulated in more detail, the instant invention serves to markedly militate against such loosening thereby alleviating the eventual need on the part of such patients for such corrective surgery.

Currently, when artificial hip protheses are implanted into the femoral bones of patients, methyl methacrylate is utilized as a bonding agent in order to bond to the protheses and at the same time to bond to the bone being implanted to thereby hold the protheses to such bone. The bonding agent functions to accomplish fixation by way of adherence to an implanted prothesis and by way of penetration of the interstitial cavitations within such bone structure while in a semi-liquid or gelatinous state such that when it hardens or cures, there is then a basis for such prosthesis fixation to such bone. Briefly stated, the femoral head and top portion of a patient's femoral bone are surgically excised away from the bone. Then a canal or shaft is bored into the bone, then the canal or shaft is filled with gelatinous methyl methacrylate, then a hip prosthesis with an artificial femoral head of its own is pressed down into the cement filled canal or shaft and found to be relatively firmly in place once said cement hardens. The cement itself is delivered into the shaft under pressure by way of syringe-like gun screwed at its base into a rigid hollow applicator tube. Once the shaft is filled with cement, a spongy tarp is placed over the filled shaft and pressure is applied down on the tarp by the surgeon in an attempt to pack the cement tightly into the shaft and hopefully ultimately into the many small interstitial cavitations lining the boundaries of the shaft.

The primary problem with respect to such loosening as referred to above lies in the bond of the device to bone by way of such cement eventually weakening with the passage of time. The integrity of such bonding is subject to the inevitability of bone growth dynamics. Bone is a living tissue and hence changes its size and shape over time thus actuating the possibility of loosening at the interstitial cavitations into which such cement would have originally been placed change in respect of size and shape. Steps have been taken to combat such a problem. One such step has been the one whereby such cement in its gelatinous state is centrifuged prior to application in order to berid the cement to the greatest possible extent of air vacuoles within it that themselves operate to compromise to no small extent the integrity of the initial bond of such cement to the bone formed by way of such cement's filling of such interstitial cavitations within such bone upon application as such. Moreover, a restrictor cap is placed at the bottom of the shaft prior to filling the shaft in order to prevent the cement from seeping into the distal part of the femur at the base of the shaft. Finally, tamping down on the bonding cement with a spongy tarp once the shaft is completely filled is yet another precaution taken to hopefully alleviate potential loosening. However, as will be noted with an eye towards the foregoing, notwithstanding such advances in respect of surgical protocol, as matters currently stand in respect of the art of inserting such protheses into bone, no effort in view of the same is now able to be made to markedly minimize such loosening by way of isolating the injected gelatinous cement from air and such air's inexorable creation of porosity within such cement that adversely affects bonding at the boundaries of the shaft and indeed even within the cement itself in terms of its relative density, also a factor in respect of such loosening until at last, at least, the above-mentioned spongy tarp is applied.

The instant device on the other hand embodies a virtually revolutionary departure from the foregoing art and for reasons that will now be set forth, is indeed, respectfully submitted, new, unique and unquestionably useful. Once the shaft has been bored and the syringe unit attached to an applicator tube after having been filled with gelatinous cement, the applicator tube is inserted into the shaft to a distance two centimeters or so above the previously inserted restrictor cap. The balloon on the end is inflated and cement is introduced into the shaft. Whereas, the balloon is inflated so as to fit tightly into the shaft, the cement is now introduced into the shaft within a closed space. This protocol causes injected cement previously rendered relatively free of air vacuoles and now exposed to virtually no air to ooze under pressure laterally much deeper than would have previously been the case with regards to the procedure previously outlined into the interstitial cavitations within such bone at the boundary of the shaft. Such deeper oozing actuates the potential for much more dependable bonding upon hardening notwithstanding bone growth dynamics over time. Injection into the closed space within the shaft below the base of the inflated balloon to the extent that injected cement is squeezed into the space and up against the base of the inflated balloon causes much greater penetration of the interstitial cavitations within the bond bonding the closed space and hence much greater bone-cement bonding due to the great increase in local pressure caused by the creation of such a closed space by and in view of the presence of the inflated balloon. Greater intra-cement bonding and concomitant density absent the potential for the erstwhile creation of air vacuoles within the cement itself will, once again, be found as well. This much more effective bonding greatly minimizes to a marked degree any potential propensity for eventual loosening. The balloon is deflated just enough to allow withdrawal of the applicator tube back up the shaft without allowing for the introduction therein of air from the top once the two centimeter long space above the restrictor cap has been filled with gelatinous cement. Withdrawal back another two centimeters in distance is followed by reinflation of the balloon to the point where the device is firmly positioned once again within the shaft. More cement is injected into this new enclosed space between the base of the maximally inflated balloon and the top surface of just previously injected cement, and the process is repeated until at last the shaft is filled as tightly as possible with such now relatively air tight gelatinous cement. The device is removed from the shaft, the spongy tarp is applied to the top layer of the cement, the prothesis is then firmly inserted into the cement rifled shaft and the cement is left to harden thereby resulting in the very firm positioning of a prothesis so anchored to bone as to most likely markedly minimize any potential propensity for eventual prosthesis loosening.

2. Prior Art

Your inventor is not aware of any prior art that anticipates the claims contemplated by the instant invention.

A SUMMARY OF THE INVENTION

A BRIEF DESCRIPTION OF THE INVENTION

The instant invention consists of inter alia a methyl methacrylate holding syringe unit, to wit, typically a holding canister equipped with plunger means, Methyl methacrylate has been the bonding cement that has been utilized for roughly the past twenty-five years or so by orthopaedic surgeons to bond artificial hip prosthesis to human bone tissue in total hip joint replacement surgical procedures. The holding canister is attached by way of a raised threaded head at its base to threading within the open head of an applicator tube with calibrated markings etched on it, the cylindrical diameter of which applicator tube is less than that of the syringe unit. The insant invention also consists of a second syringe unit cylindrical in shape and amenable to being filled with a fluid such as air or saline solution which is equipped at its base with a one-way valve receptacle for receipt of a one-way valve unit affixed to a fluid delivery system, to wit, cylindrically shaped flexible tubing. The second syringe unit is connected by way of such flexible tubing to an inflatable balloon. The inflatable balloon is located at or about the tip of the applicator tube attached as noted above to the methyl methacrylate holding syringe unit. Such flexible tubing serves to extend into an entry hole located in the walling of the applicator tube which hole marks the entryway to a second but separate lumen that is closed but for an exit hole at its end. This second lumen runs for a distance along the length of the lumen of the applicator tube but for a distance less than the whole of such length such that fluid from the second syringe unit is force into the tubing can pass therefrom through the entry hole and can exit the second lumen through the exit hole and into the above-mentioned balloon.

THE OBJECT OF THE INVENTION

The object of the instant invention is to militate to the fullest possible extent against the possibility of loosening of an implanted artificial hip prothesis and the invariably concomitant need for expensive and at least temporarily debilitating corrective surgery. The enhanced obviation of the potential need for such corrective surgery respectfully submitted, renders the instant invention unquestionably new, useful and unique.

A DESCRIPTION OF THE PREFERRED EMBODIMENT

Figure 1:
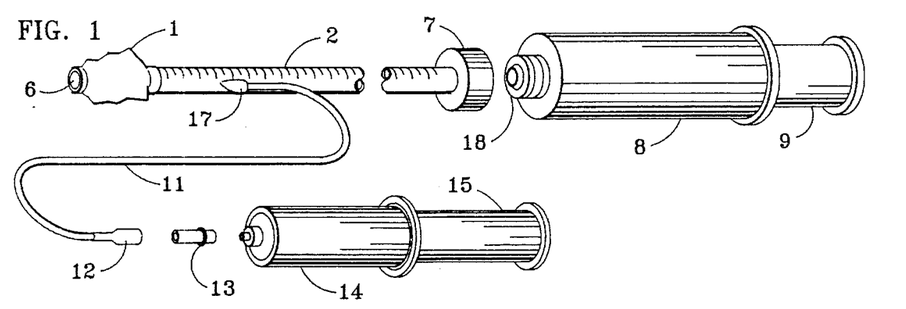
FIG. 1 is an exploded plan view of the instant invention.
Figure 2:
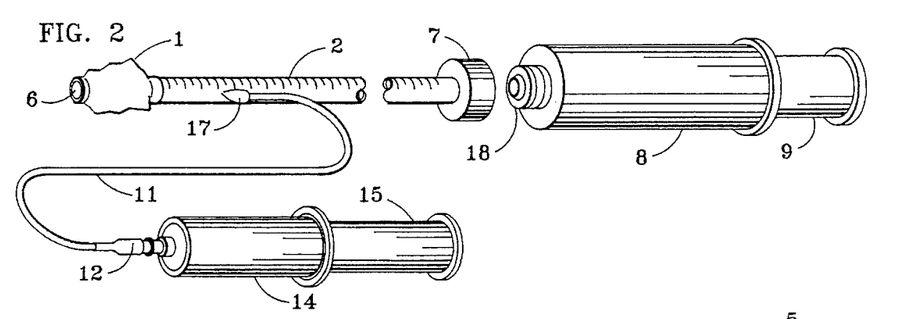
FIG. 2 is a partially exploded plan view of the intact instant invention.
Figure 3:
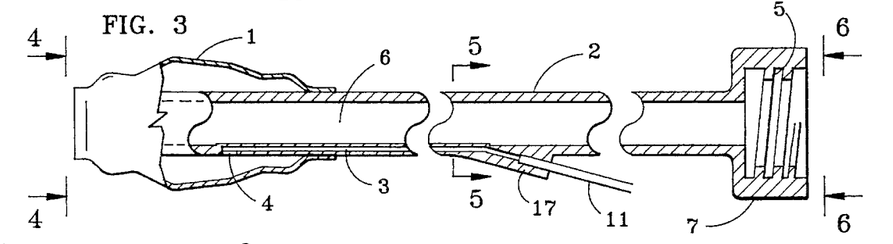
FIG. 3 is a longitudinal sectional view of the applicator tube component of the instant invention with the invention's attached balloon component shown in a deflated state.
Figure 4:
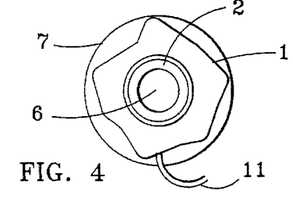
FIG. 4 is a bottom end view of the instant invention.
Figure 5:
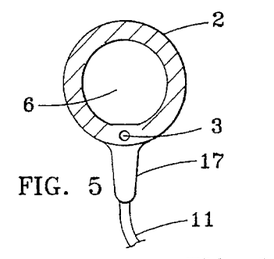
FIG. 5 is a cross-sectional view of a portion of the applicator tube component of the instant
Figure 6:
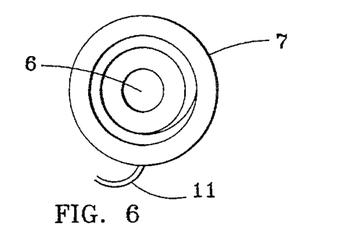
FIG. 6 is an on end top view of the applicator tube component of the instant invention. invention.
Figure 7:
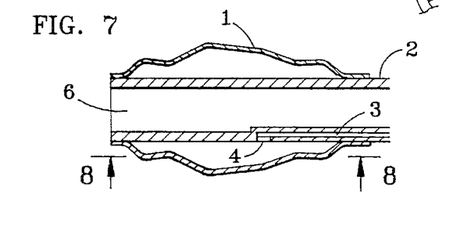
FIG. 7 is an enlarged cutaway view of a portion of the applicator tube component of the instant invention.
Figure 8:
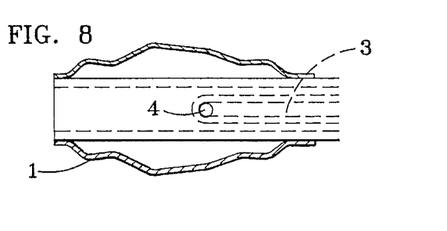
FIG. 8 is an enlarged sectional view of the bottom side of that portion of the applicator tube component of the instant invention shown in FIG. 7.
Figure 9:
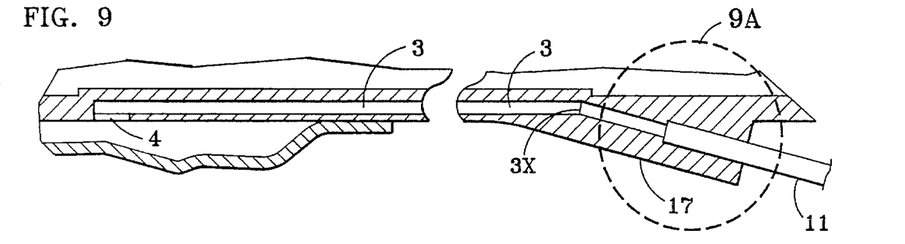
FIG. 9 is an enlarged sectional view of that portion of the applicator tube component of the instant invention that is characterized by the presence of a separate tube carrying lumen also shown.
Figure 9A:
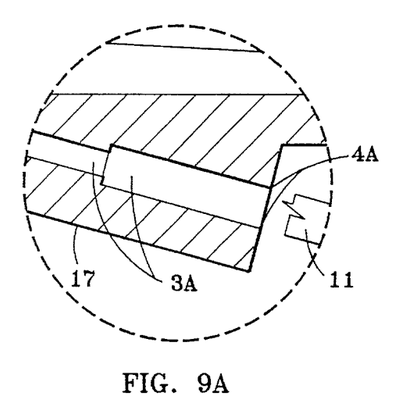
FIG. 9A is an isolated enlarged sectional view of a portion of FIG. 9.
Figure 10:
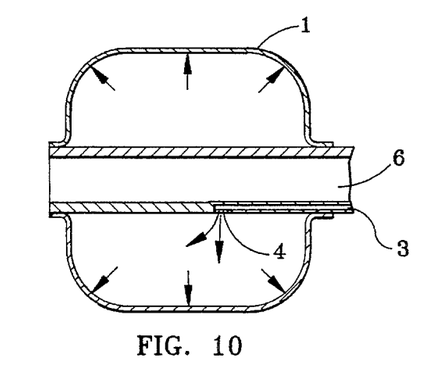
FIG. 10 is an isolated view of the instant invention's balloon component shown as inflated.
Figure 11:
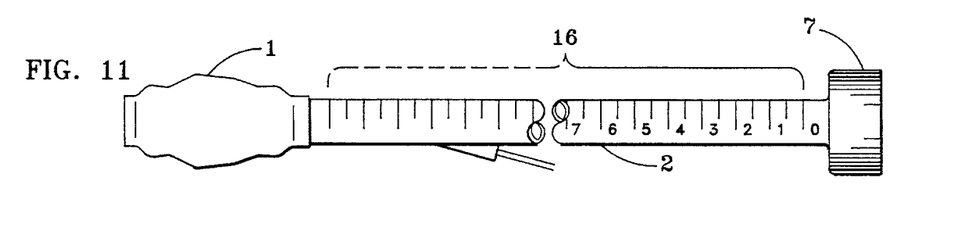
FIG. 11 is a lateral plan view of one side of the applicator tube component of the instant invention showing enumerated distance markings along the shaft of the tube leading to the locus of the head of the tube.
Figure 12:
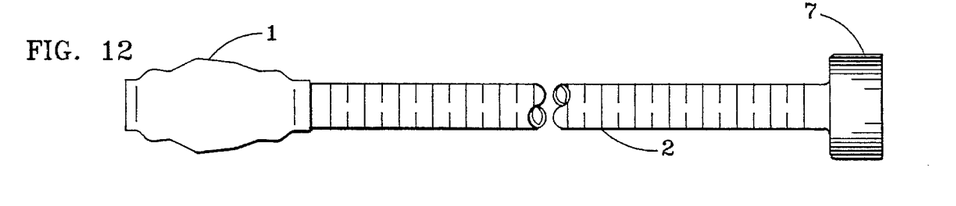
FIG. 12 is a top or a bottom plan view of the applicator tube component of the instant invention.
Figure 13:
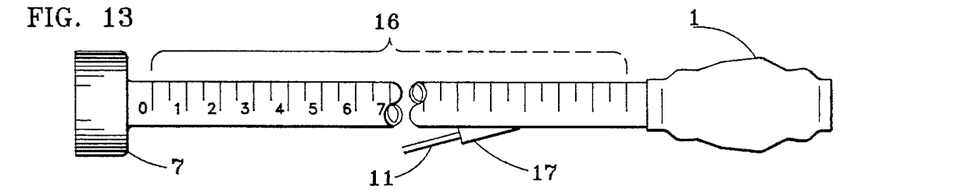
FIG. 13 is a lateral plan view of the other side of the applicator tube component of the instant invention showing enumerated distance markings along the shaft of the tube leading to the locus of the head of the tube.
Figure 14:
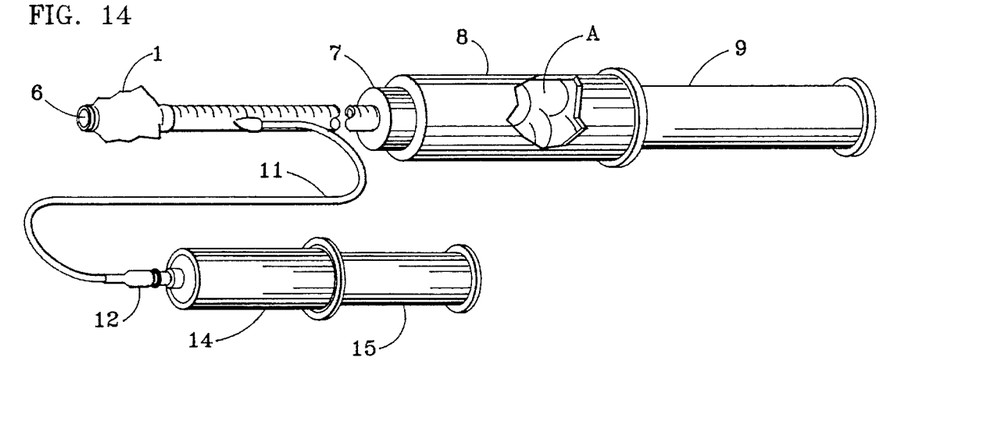
FIG. 14 is a plan view of the instant invention showing gelatinous methyl methacrylate within the body of the instant invention's syringe component.
Figure 15:
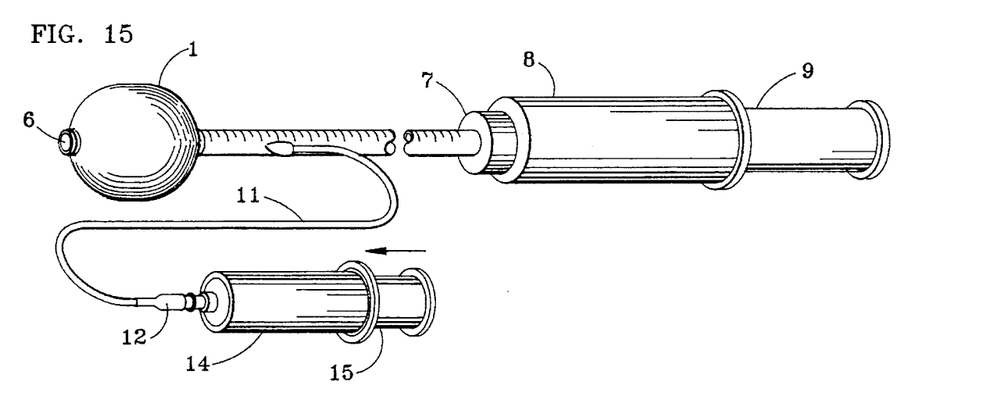
FIG. 15 is a plan view of the instant invention showing its balloon component as inflated.
Figure 16:
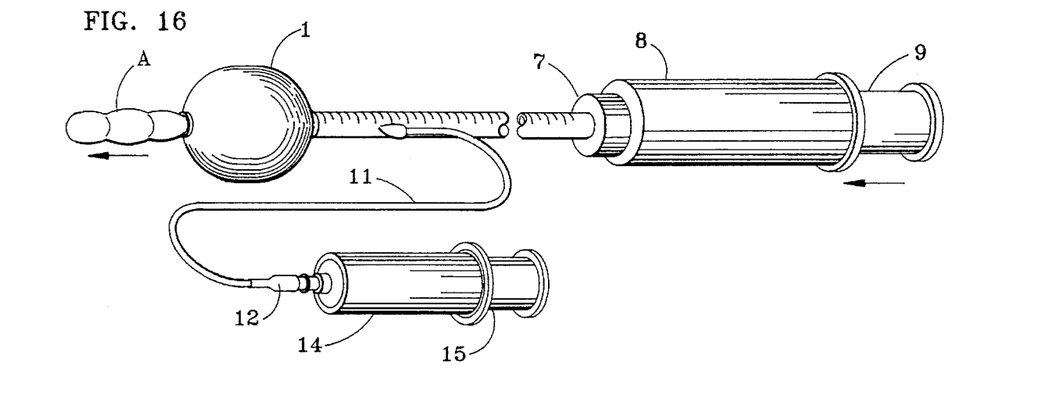
FIG. 16 shows cement being pushed through the bottom tip of the applicator tube component of the instant invention as pressure is exerted down on the plunger portion of the instant invention's syringe component.
Figure 17:
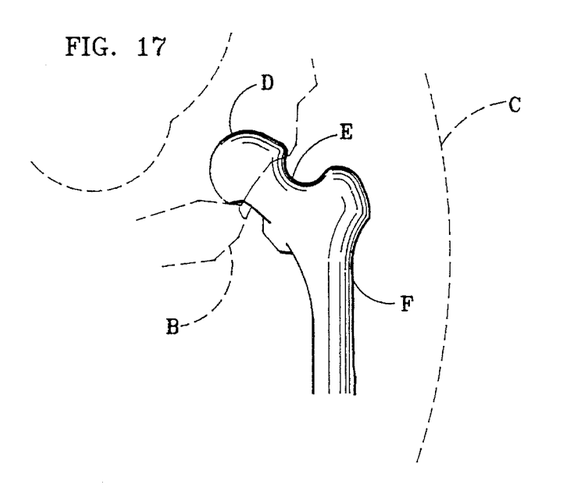
FIG. 17 shows an intact human femur held by way of its femoral head within the acetabulum of a human hip.
Figure 18:
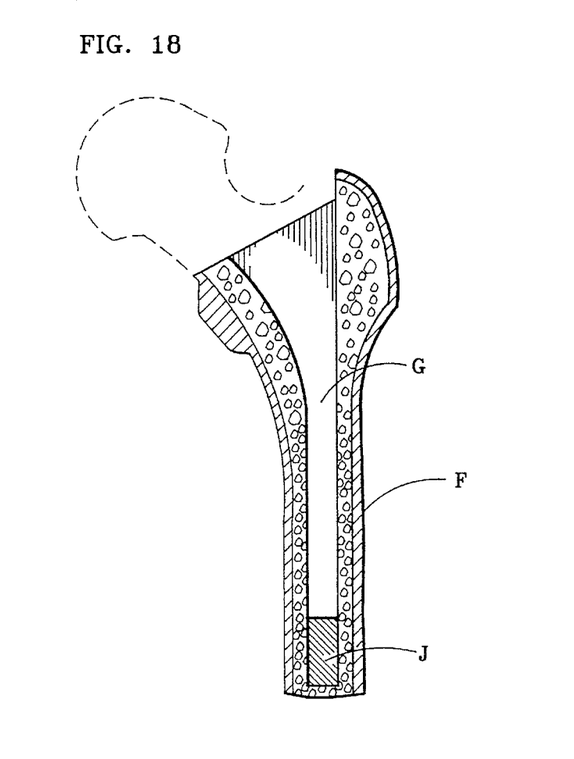
FIG. 18 shows in sectional view a human femur after its head has been surgically removed, a shaft bored into it and a restrictor cap placed into the bottom of the shaft.
Figure 19:
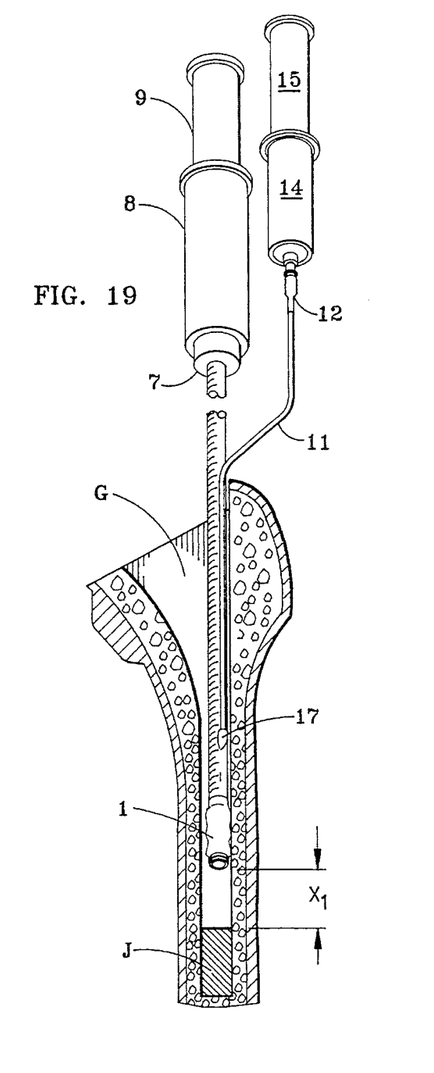
FIG. 19 shows the manner of insertion of the applicator tube component of the instant invention with balloon component attached thereto into the bored femoral shaft to a point a short distance above the location of the restrictor cap.
Figure 20:
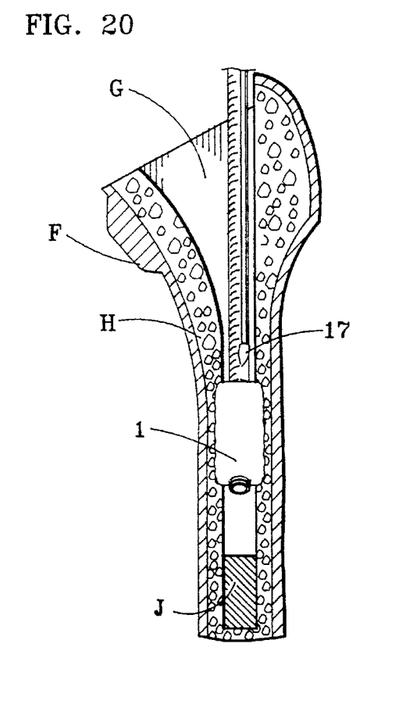
FIG. 20 shows in isolation the applicator tube component and attached balloon component within the bored shaft positioned a short distance above the location of the restrictor cap.
Figure 21:
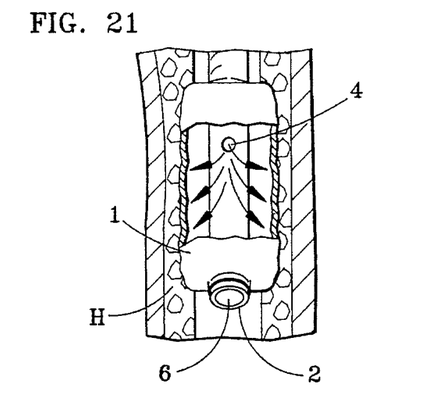
FIG. 21 shows in isolation a cutaway view of the invention's balloon component in-situ being inflated with fluid.
Figure 22:
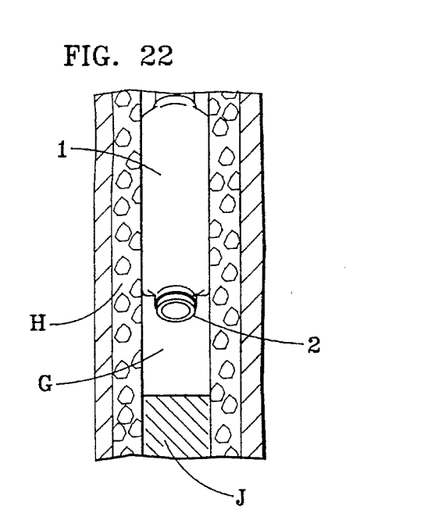
FIG. 22 shows in isolation, a closed spaced within a bored shaft between the restrictor cap and the base of the instant invention's balloon component in an inflated state.
Figure 23:
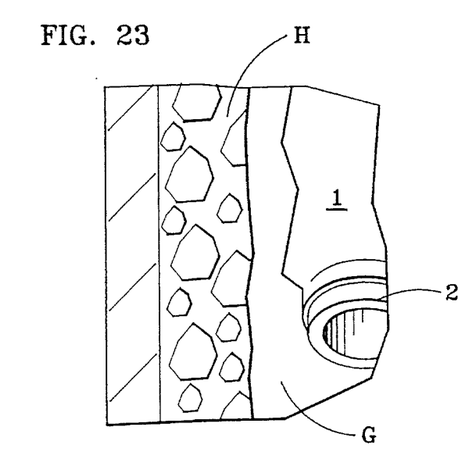
FIG. 23 is a close-up view of part of the lower portion of the instant invention's balloon component in a deflated state near the end tip of the invention's applicator tube component.
Figure 24:
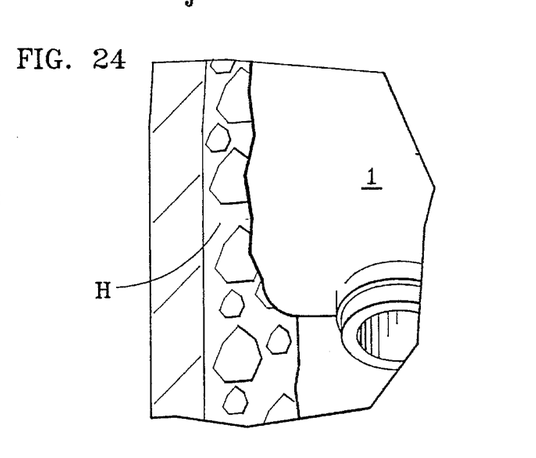
FIG. 24 shows what is seen in FIG. 23 except that the part of the lower portion of the balloon component of the instant invention is shown in an inflated state.
Figure 25:
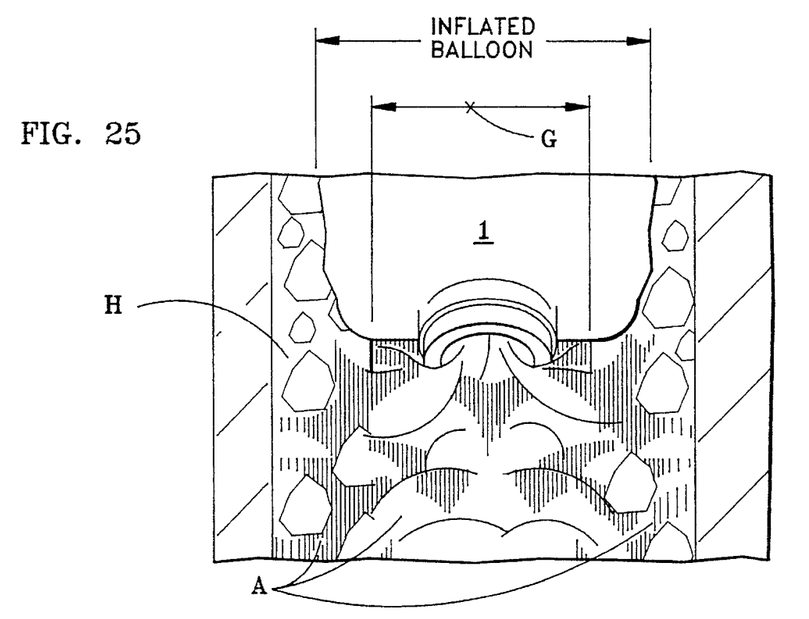
FIG. 25 shows in close-up view gelatinous methyl methacrylate emanating under pressure from the end tip of the instant invention's applicator tube component into the closed space formed by the invention's balloon component in an inflated state.
Figure 26:
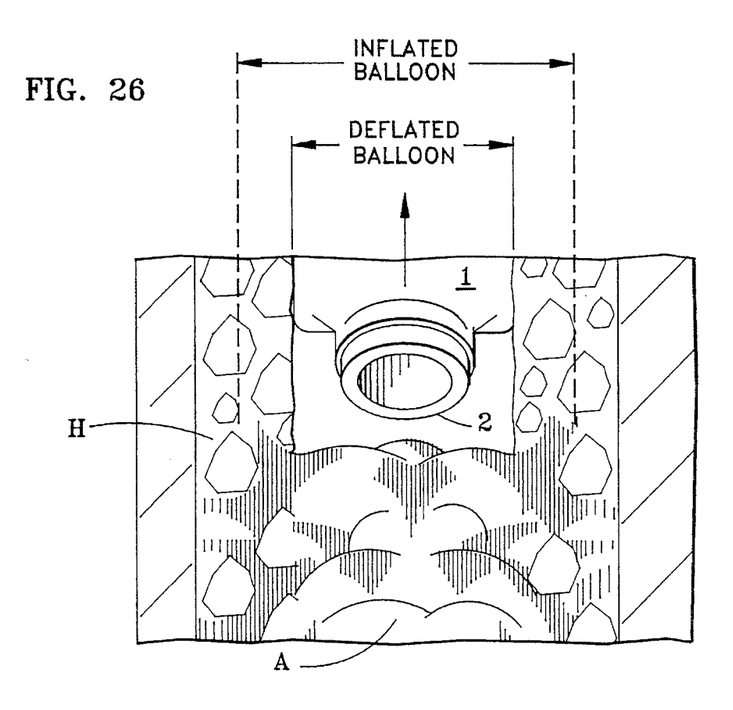
FIG. 26 shows what is seen in FIG. 25 except that here gelatinous methyl methacrylate has been shown injected into the closed space and is here shown having seeped deeply into the interstitial cavitations within bone on the boundary of the bored shaft, and the balloon component of the instant invention is shown partially deflated and being withdrawn in the direction of the arrow from its former location to a point higher up the shaft.
Figure 27:
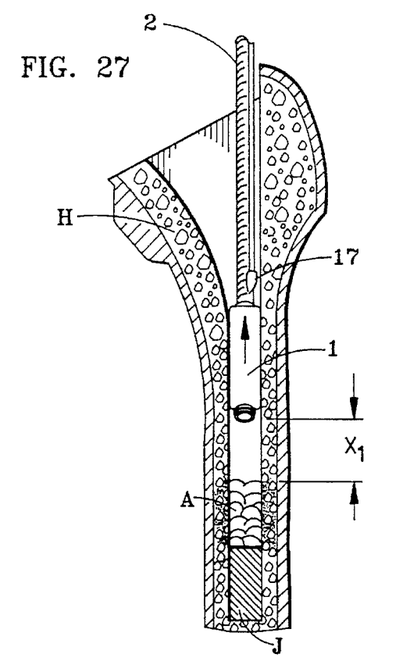
FIG. 27 shows retraction of the tip of the applicator tube component of the instant invention back a short distance along the bored shaft after some gelatinous methyl methacrylate has been injected into the shaft.
Figure 28:
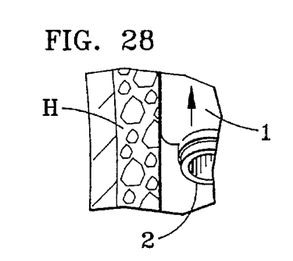
FIG. 28 is a close-up view of the process of retracting the instant invention with only a relatively small amount of deflation of the instant invention's balloon component.
Figure 29:
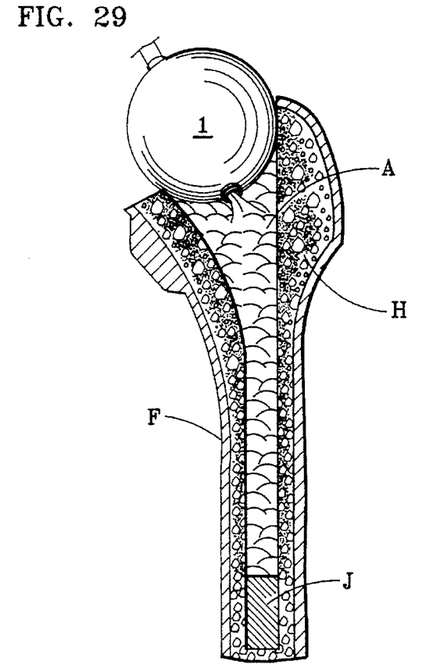
FIG. 29 is a sectional view of a fully cemented femoral shaft and inflated balloon.
Figure 30:
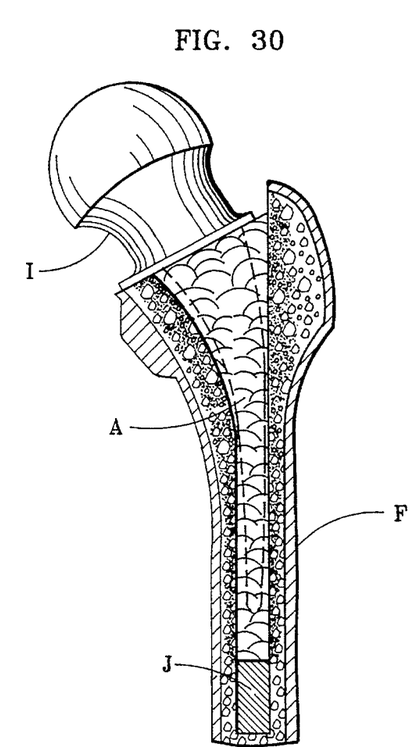
FIG. 30 shows an artificial hip prothesis inserted into the fully cemented femoral shaft.

The instant invention is shown in exploded plan view in FIG. 1. A plan view of the intact instant invention but for arbitrary length of its applicator tube component 2 is shown in FIG. 2. FIG. 4 is an end view of the bottom of the applicator tube component 2 of the invention with permanently attached balloon component i shown in a deflated state. FIG. 3 shows in sectional view the applicator tube component 2. FIG. 6 is a top end view of component 2 where there is to be noted the outer circumference of the head 7 of component 2. A patient in need of a surgical procedure to be fitted with an artificial hip prothesis with an outer body C, pelvis B, femoral head D on femoral neck E of a femur F as shown in FIG. 17 is subjected to a surgical excision of head D and neck E and then the boring of shaft G into the body of femur F as shown in FIG. 18. Then, restrictor cap J is fitted firmly to the bottom of shaft G. Ultimately, there will be fitted into shaft G once filled with methyl methacrylate bonding cement A, hip prothesis I as shown in FIG. 30. Once shaft G is bored into femur F, applicator tube component 2 fitted with balloon 1 is inserted into shaft G as shown in FIG. 19. Before such insertion takes place however, gelatinous methyl methacrylate Cement A is centrifuged to remove as much air therefrom as possible and is then placed into first syringe body 8. First syringe plunger 9 is then inserted into body 8 as shown in FIGS. 1, 2 and 15. Then internal threading 5 of tube cap 7 is screwed to threading 18 at the base of the first syringe body 8 as shown in FIG. 1 to form the intact unit seen in FIG. 2. Upon insertion, plunger 15 within second syringe body 14 filled previously with fluid such as a saline solution is pushed down thereby causing fluid to pass from body 14 through one way valve 13 seen in FIG., 1, through tygon connecting tube 12 into fluid carrying tubule 11, into closed lumen 3 adjacent lumen 6 of applicator tube 2 via portal 17 constructed on and along the shaft of tube 2, out hole 4 and into balloon 1 thereby inflating balloon 1 permanently affixed to the shaft of tube 2 near its bottom hollow tip. Reference to FIGS. 2 and 3 enables one to view all of the foregoing components. FIG. 10 shows fluid passing from hole 4 into balloon 1 causing it to be inflated. FIG. 5 is a cross sectional view of tube 2, lumen 6, closed lumen 3, portal 17 and tubule 11 just above the upper boundary of balloon 1 permanently affixed to tubule 2. FIG. 7 and FIG. 8 show in differing and more detailed views the positional relationships as between balloon 1, lumen 6, hole 4 and closed lumen 3. FIG. 9 shows in sectional view the positional relationships of hole 4, closed lumen 3, portal 17 and tubule 11. A lumen 3A encased by the walling of portal 17 is also shown in FIG. 9 turning directly into lumen 3 at point 3X. Also shown in FIG. 9 as well as in FIG. 9A is a hole 4A in portal 17 through which tubule 11 is passed directly into lumen 3A. The purpose of an outer portal 17 and a closed lumen 3 is to separate and isolate tubule 11 and the fluid contained therein earmarked for the interior of balloon 1 from the methyl methacrylate bonding cement ultimately to be found within lumen 6 and its potentially corrosive effects on tubule 11 not to mention capacity due to its presence for interfering with the ready flow of such fluid to or form the interior of balloon 1. Balloon 1 is thereby inflated so as to completely fill the spance of shaft G some two centimeters or so above the location of restrictor cap J. FIG. 14 shows methyl methacrylate bonding cement A within first syringe body 8 as the instant invention is readied for use. FIG. 15 shows balloon 1 in an inflated state with pressure in the direction of the arrow therein depicted having been applied to plunger 15. FIG. 16 shows extrusion of cement A through the bottom tip of tube 2 when downward pressure is applied to plunger 9 in the direction of the arrow therein shown. FIG. 19 shows balloon 1 and tube 2 within shaft G just prior to inflation of balloon 1. FIG. 21 shows fluid entering balloon 1 in operational position in order to inflate it and FIG. 22 shows in isolated view inflated balloon 1 above a closed space within shaft G between balloon 1 and restrictor cap J. FIG. 20 is a panoramic view of what is seen in FIG. 22 showing as well in longitudinal sectional view, the boundary of shaft G within femur F surrounded by interstitial bone cavitations H. FIG. 23 shows deflated balloon 1 close-up within shaft G in proximity to interstitial bone cavitations H. FIG. 24 is likewise a close-up view of what is seen in FIG. 22. FIG. 25 shows in close-up view, cement A being injected into the closed space of shaft G and emanating laterally under injection pressure relatively deeply into interstitial bone cavitations H. FIG. 26 shows partial deflation of balloon 1 within the closed space after injection of cement A into the closed space and in turn cavitations H. Such partial deflation is accomplished by drawing back plunger 15 in the direction opposite to that of the arrow shown in FIG. 16. After such partial deflation as also seen in a different perspective close-up in FIG. 28, the balloon 1 and tube 2 component of the instant invention is withdrawn within shaft G for a distance of two centimeters or so to now form as per FIG. 27, a closed space now between the bottom of balloon 1 and the cement A previously injected into shaft G just above restrictor cap J. FIGS. 11, 12 and 13 show calibrated markings on applicator tube 2 serving to guide a surgeon in respect of far to withdraw tube 2 between the successive injections of cement A. Another portion of cement A is injected as before into this new closed space after balloon 1 is reinflated as before so as to fit quite tight once again the boundaries of shaft G. The process of inflation, injection, partial deflation, reinflation and reinjection is repeated until at last shaft G is completely filled with cement A as shown in FIG. 29. Dark stippling along the boundaries of shaft G in FIGS. 27, 29 and 30 represents bonding cement A oozing under pressure deeply into cavitation spaces H. Finally as per FIG. 30, a prosthesis I is inserted into the cement A in filled shaft G and is firmly anchored within femur F once cement A cures and hardens.

The purpose of the closed space within shaft G between the base of balloon 1 in an inflated state and everything below it within shaft G is to form a relatively airtight pocket within which to inject cement A so as to ensure that it will penetrate more deeply than otherwise into interstitial bony cavitations H circumscribing the whole of the boundary of the closed space than would be the case if, as with the way cement is currently injected into such shafts, such closed space were non-existent due to the lack of an inflatable balloon 1 near the tip of the applicator tube 2 through which such cement A is currently injected. Moreover, such closed space created by way of inflation of balloon 1 prevents air from reaching gelatinous cement A once injected thereby ensuring that not only is cement to bone bonding greatly enhanced but likewise intracement density is maintained to the greatest possible extent as well. In this way, compactness of cement is maximized and the integrity of the prothesis anchoring process is correlatively maximally preserved. Another embodiment of the instant invention would be one characterized by the presence of a lumen carrying fluid from tubule 11 located outside of rather than within tube applicator 2. In the case of this embodiment, a hole at the end of such an exterior lumen would lead directly to balloon 1 such that tubule 11 would pass through the whole of such exterior lumen directly into balloon 1. Still yet, another embodiment is one whereby tubule 11 is attached directly to balloon 1.

In closing, respectfully submitted, the instant invention will unquestionably prove to greatly benefit patients who are initially fitted with hip prostheses I in terms of greatly ensuring that they will not need replacement surgery in future years thereby obviating not only the trauma to such patients from such additional surgery but also the relatively tremendous cost obviously associated with the performance of such additional surgery.

What is claimed is:

1. A biomedical cement bonding enhancer, comprising:

a) a first hollow syringe body containing gelatinous cement;

b) a plunger fitted to said first hollow syringe body;

c) an opening at the base of said first hollow syringe body;

d) a hollow extension of said opening circumscribed by screw threading means permanently affixed to the base of said first hollow syringe body;

e) a long, hollow, rigid tube with a first open end and a second open end;

f) a hollow cap containing threading about the interior walling of said cap which said cap is permanently affixed to said first open end of said long, hollow, rigid tube which said threading serves to receive said screw threading means;

g) inflatable material with two open ends in the shape of a hollow cylinder permanently affixed at each of said two open ends of said inflatable material to that portion of the exterior surface of said long, hollow, rigid tube in proximity to said second open end of said long, hollow, rigid tube such that said inflatable material completely circumscribes said portion of the said exterior surface of said long, hollow, rigid tube;

h) a second hollow syringe body;

i) an opening at the base of said second hollow syringe body;

j) a plunger fitted to said second hollow syringe body;

k) a hollow extension of said opening at the base of said second hollow syringe body which said hollow extension is permanently affixed to said base of said second hollow syringe body;

l) a hollow valve unit fitted at a first end to said hollow extension of said opening at the base of said second hollow syringe body;

m) a piece of flexible tubing;

n) a hollow connector connecting a first end of said piece of flexible tubing to the second end of said hollow valve unit;

o) an open portal with walling which said open portal is molded to the exterior surface of said long, hollow, rigid tube;

p) an enclosed hollow canal encased by the said walling of said open portal leading from a first hole cut through the wall of said long, hollow, rigid tube to a point in the proximity of the opening of said open portal which said enclosed hollow canal serves to receive the second end of said piece of flexible tubing;

q) a second enclosed hollow canal leading from said first hole cut through the wall of said long, hollow, rigid tube and running along the interior surface of said long, hollow, rigid tube to a second hole in the said wall of said long, hollow, rigid tube which said second hole is located within that portion of said wall circumscribed totally by said inflatable material.

2. A method for applying bonding cement to a shaft bored into a human femur for the purpose of anchoring an artificial hip prosthesis, comprising the steps of:

a) fitting a restrictor cap snug into the bottom of said shaft;

b) permanently affixing both ends of an inflatable material in the shape of a hollow cylinder to the exterior surface of a long, hollow, rigid tube with a first open end and a second open end near said first open end of said long, hollow, rigid tube;

c) connecting said second open end of said long, hollow, rigid tube to a raised opening in the base of the body of a first hollow syringe unit;

d) connecting a valve in the exterior surface of said inflatable material to a first of two open ends of flexible hollow tubing;

e) connecting a second of said two open ends of said flexible hollow tubing to a hollow connector;

f) connecting said hollow connector to a raised opening in the base of a second hollow syringe unit;

g) filling said first hollow syringe unit with bonding cement;

h) filling said second hollow syringe unit with a fluid;

i) inserting said first open end of said long, hollow, rigid tube into said bored shaft in proximity to said restrictor cap;

j) placing a fluid pushing plunger into said second hollow syringe unit;

k) forcing with downward pressure on said fluid pushing plunger said fluid via said flexible hollow tubing into said inflatable material and inflating said inflatable material until the said inflatable material in a fully inflated state completely presses everywhere very tightly against the bony walling of said bored shaft;

l) placing a bonding cement pushing plunger into said first hollow syringe unit;

m) forcing with downward pressure on said bonding cement pushing plunger, a quantity of said bonding cement into a first closed space within said bored shaft between said inflatable material in said fully inflated state and said restrictor cap via said long, hollow, rigid tube;

n) drawing back on said fluid pushing plunger so as to slightly deflate said inflatable material;

o) withdrawing said first end of said long, hollow, rigid tube a short distance from its location within said bored shaft when said bonding cement was last injected into said first closed space;

p) pushing down again on said fluid pushing plunger so as to once again inflate said inflatable material to the extent that said inflatable material in said fully inflated state completely presses everywhere very tightly against the bony walling of said shaft;

q) forcing with downward pressure on said bonding cement pushing plunger a quantity of said bonding cement into a new closed space within said bored shaft between said inflatable material in said fully inflated space and the top surface of said last injected bonding cement;

r) repeating steps k, l, m, n, o, p, and q successively until said bored shaft is completely filled with said bonding cement;

s) repeating steps n, o, p and q successively until said bored shaft is completely filled with said bonding cement.

3. The method of claim 2 whereby said bonding cement is methyl methacrylate.

4. The method of claim 2 whereby said fluid is a liquid solution.

5. The method of claim 2 whereby said fluid is in a liquid state.

6. The method of claim 2 whereby said fluid is in a gaseous state.

7. A method for applying bonding cement to a shaft bored into a human femur for the purpose of anchoring an artificial hip prothesis comprising the steps of:

a) fitting a restrictor cap snug into the bottom of said shaft;

b) permanently affixing both ends of an inflatable material in the shape of a hollow cylinder to a first portion of the exterior surface of a long, hollow, rigid, bicannulated tube with a first open end and a second open end near said first open end of said long, hollow, rigid bicannulated tube and completely circumscribing with said permanently affixed inflatable material said first portion of said exterior surface after first cutting a first hole into said first portion of said long, hollow, rigid bicannulated tube as is completely circumscribed externally by said permanently affixed inflatable material and circumscribed internally by the enclosing walling of one of the two canals within said long, hollow, rigid bicannulated tube;

c) sealing at said first open end of and in proximity to mid second open end of said long, hollow, rigid, bicannulated tube a first canal of said long, hollow, rigid, bicannulated tube, the external walling of which said first canal contains said first hole;

d) cutting a second hole into the portion of said exterior surface of said long, hollow, rigid, bicannulated tube further from said first end of said long, hollow, rigid, bicannulated tube than the end of said inflatable material that is the farthest of said both ends of said inflatable material from said first end of said long, hollow, rigid, bicannulated tube which said second hole leads directly into said first canal;

e) connecting said second open end of said long, hollow, rigid, bicannulated tube to a raised opening in the base of the body of a first hollow syringe unit;

f) connecting a first of two open ends of flexible hollow tubing to the whole boundary of said second hole;

g) connecting a second of said two open ends of said flexible hollowing tubing to a hollow connector;

h) connecting said hollow connector to a raised opening in the base of a second hollow syringe unit;

i) filling said first hollow syringe unit with bonding cement;

j) filling said second hollow syringe unit with a fluid;

k) inserting said first end of said long, hollow, rigid tube into said bored shaft in proximity to said restrictor cap;

l) placing a fluid pushing plunger into said second hollow syringe unit;

m) forcing with downward pressure on said fluid pushing plunger said fluid via said flexible hollow tubing into said inflatable material and inflating said inflatable material until said inflatable material in a fully inflated state completely presses everywhere very tightly against the bony walling of said bored shaft;

n) placing a bonding cement pushing plunger into said first hollow syringe unit;

o) forcing with downward pressure on said bonding cement pushing plunger a quantity of bonding cement into a first closed space within said bored shaft between said inflatable material in said fully inflated state and said restrictor cap via said long, hollow, rigid tube;

p) drawing back on said fluid pushing plunger so as to slightly deflate said inflatable material;

q) withdrawing said first end of said long, hollow, rigid tube a short distance from its location within said bored shaft when said bonding cement was last injected into said first closed space;

r) pushing down again on said fluid pushing plunger so as to once again inflate said inflatable material to the extent that said inflatable material in said fully inflated state completely presses everywhere very tightly against the bony walling of said shaft;

s) forcing with downward pressure on said bonding cement pushing plunger a quantity of said bonding cement into a new closed space within said bored shaft between said inflatable material in said fully inflated space and the top surface of said last injected bonding cement;

t) repeating steps m, o, p, q, r, and s successively until said bored shaft is completely filled with said bonding cement u) repeating steps p, q, r and s successively until said bored shaft is completely filled with said bonding cement.

8. The method of claim 7 whereby said bonding cement is methyl methacrylate.

9. The method of claim 7 whereby said fluid is a liquid solution.

10. The method of claim 7 whereby said fluid is in a liquid state.

11. The method of claim 7 whereby said fluid is in a gaseous state.

* * * * *